United States Patent
Weissman et al.

(10) Patent No.: US 10,538,754 B2
(45) Date of Patent: Jan. 21, 2020

(54) METHOD FOR PREPARATION OF THROMBIN

(71) Applicants: Omrix Biopharmaceuticals Ltd., Rehovot (IL); Guangzhou Bioseal Biotech Co., Ltd., Guangzhou (CN)

(72) Inventors: Lior Weissman, Ness-Ziona (IL); Dana Sella, Rehovot (IL); Israel Nur, Nes-Ziona (IL); Caixia Jiang, Guangzhou (CN); Baochang An, Guangzhou (CN)

(73) Assignees: Omrix Biopharmaceuticals Ltd., Rehovot (IL); Guangzhou Bioseal Biotech Co., Inc.; Guangzhou Science Co., Inc.

( * ) Notice: Subject to any disclaimer, the term of this patent is extended or adjusted under 35 U.S.C. 154(b) by 30 days.

(21) Appl. No.: 15/547,839

(22) PCT Filed: Feb. 6, 2015

(86) PCT No.: PCT/CN2015/072436
§ 371 (c)(1),
(2) Date: Aug. 1, 2017

(87) PCT Pub. No.: WO2016/123804
PCT Pub. Date: Aug. 11, 2016

(65) Prior Publication Data
US 2018/0016567 A1    Jan. 18, 2018

(51) Int. Cl.
*C12N 9/64* (2006.01)
*G01N 33/84* (2006.01)
*G01N 33/86* (2006.01)
*C12N 9/74* (2006.01)

(52) U.S. Cl.
CPC .... *C12N 9/6429* (2013.01); *C12Y 304/21005* (2013.01); *G01N 33/84* (2013.01); *G01N 33/86* (2013.01); *G01N 2333/745* (2013.01)

(58) Field of Classification Search
None
See application file for complete search history.

(56) References Cited

U.S. PATENT DOCUMENTS

| | | | | |
|---|---|---|---|---|
| 3,947,378 A | * | 3/1976 | Babson | G01N 33/96 436/16 |
| 4,334,018 A | | 6/1982 | Kirchhof | |
| 4,789,545 A | | 12/1988 | Woods et al. | |
| 5,094,960 A | | 3/1992 | Bonomo | |
| 2005/0265989 A1 | | 12/2005 | Manseth | |

FOREIGN PATENT DOCUMENTS

| | | |
|---|---|---|
| CN | 101371921 A | 7/2018 |
| DE | 2757992 A1 | 12/1977 |
| EP | 0680763 A2 | 11/1995 |
| JP | H08/40928 A | 2/1996 |
| KR | 198902070 B1 | 7/2018 |

OTHER PUBLICATIONS

Biggs, et al., The Measurement of Prothrombin in Plasma A Case of Prothrombin Deficiency, J. clin.Palh, 1953, pp. 1-9, vol. 6 Issue 15.
Fantl, et al., The Significance of Prothrombin Accelerator in the Thrombin Formation by Russell Viper Venom, Australian Journal of Experimental Biology and Medical Sciences, 1949, pp. 197-205, vol. 27, No. 2.
Fujimara, et al., A Simultaneous Purification of Human Prothrombin and Factor IX, Blood & Vessel, 1982, pp. 63-71, vol. 13, Issue 32.
International Search Report dated Nov. 19, 2015 for Application No. PCT/CN2015/072436.
Turaga, et al., Rapid Purification of High Purity Thrombin and Preparation of a Novel Hemostat for Clinical Purposes, Indian J. Hematol. Blood Transfus, 2008, pp. 54-58, vol. 24, Issue 2.
Zhongmin, et al., Purification and Activity Identification of Thrombin from Bovine Plasma, Journal of China Medical University, 1994, pp. 436-437, vol. 23, No. 5.

* cited by examiner

*Primary Examiner* — Suzanne M Noakes
(74) *Attorney, Agent, or Firm* — David R. Crichton

(57) ABSTRACT

The present invention is directed to methods for the production of thrombin from a source of prothrombin using a given $BaSO_4$ reagent as an adsorbent of prothrombin as well as methods for evaluating the suitability of a given $BaSO_4$ reagent for use in preparation of thrombin. In at least one embodiment, the method includes contacting a sample of the given $BaSO_4$ reagent with a source of prothrombin to obtain $BaSO_4$-adsorbed prothrombin, and subsequently evaluating the pro-coagulant activity of the $BaSO_4$-adsorbed prothrombin. In another embodiment, the method includes the step of evaluating relative to the pro-coagulant activity of normal mammalian plasma.

18 Claims, 3 Drawing Sheets

METHOD FOR PREPARATION OF THROMBIN

FIELD OF THE INVENTION

The invention relates to the field of thrombin production, and more specifically to methods for evaluating the suitability of a given $BaSO_4$ reagent for use as a prothrombin adsorbent in the preparation of thrombin.

BACKGROUND OF THE INVENTION

Thrombin is a serine protease that facilitates blood clotting by catalyzing the conversion of fibrinogen to fibrin. Thrombin is also responsible for activating platelets and indirectly responsible for regulation of its own production and inhibition through multiple proteolytic feedback mechanisms. Thrombin is also involved in activation of factor VIII, factor V, factor XI, factor XIII and protein C. Thrombin is widely used in clinical applications as a coagulation factor to staunch bleeding of wounds by conversion of fibrinogen to fibrin. Thrombin is a common component of surgical dressings, and has been used in combination with fibrinogen and other coagulation proteins in two-component hemostatic systems such as fibrin glues, adhesives, and sealants.

Thrombin is produced by proteolytic activation of the precursor (zymogen) prothrombin. For the production of thrombin, prothrombin must be cleaved at two sites generating intermediate products. The conversion of prothrombin to thrombin in the body is catalyzed by the prothrombinase complex which includes activated Factor X and Factor V and assembles on negatively charged phospholipid membranes in the presence of calcium ions.

Thrombin may be manufactured from prothrombin by contacting a source of prothrombin (such as blood plasma or a blood fraction), with a solid adsorbent capable of adsorbing the prothrombin from the source of prothrombin, for example barium sulfate ($BaSO_4$). The solid adsorbent is typically washed using a washing solution to remove contaminants such as unbound proteins, and subsequently the prothrombin is eluted therefrom using an elution solution. Subsequent to additional optional purification and processing steps, the eluted prothrombin can be converted to thrombin by activation using an activator, e.g., calcium ions. It has been reported that significant differences in yield of thrombin from a given volume of a source of prothrombin are found when using different $BaSO_4$ reagents, such as $BaSO_4$ reagents obtained from different manufacturers or even different batches of reagent produced by a specific manufacturer.

It has been proposed in reports that differences in thrombin yield are at least partially attributable to variations in adsorption of prothrombin by different $BaSO_4$ reagents and that adsorption capacity is a key factor in the choice of $BaSO_4$ reagent for prothrombin adsorption. Surgenor and Neortker (1952) stated that certain $BaSO_4$ reagents are more effective than others in adsorption of prothrombin from plasma while Voss D. (1965) noted that when using different $BaSO_4$ reagents for adsorption of prothrombin complex, significant differences were found in the amount of $BaSO_4$ needed to adsorb the same amount of prothrombin complex and speculated that this was due to differences in their crystal structure. However, in the Applicant's case, the morphology of different batches of $BaSO_4$ have been tested and no significant differences were determined. Also some ions, e.g. $Ca^{2+}$, were reported to contribute to different adsorption rates for different $BaSO_4$ batches, and in this case, the presence of $Ca^{2+}$ in different batches of $BaSO_4$ was not significantly different either.

Thrombin manufacturers attempt to increase thrombin yield by resorting to a trial and error method of selecting a suitable $BaSO_4$ reagent from among multiple different $BaSO_4$ reagents.

SUMMARY OF THE INVENTION

The invention, in some embodiments thereof, relates to method for the production of thrombin from a source of prothrombin using a given $BaSO_4$ reagent as an adsorbent of prothrombin as well as methods for evaluating the suitability of a given $BaSO_4$ reagent for use in preparation of thrombin by contacting the given $BaSO_4$ reagent with a source of prothrombin to obtain $BaSO_4$-adsorbed prothrombin, and evaluating the pro-coagulant activity of the $BaSO_4$-adsorbed prothrombin, in some embodiments, relative to the pro-coagulant activity of normal mammalian plasma.

Contacting is used herein in its broadest sense and refers to any type of combining action which e.g. brings the prothrombin source into sufficiently close proximity with $BaSO_4$ such that a binding interaction will occur between $BaSO_4$ and the prothrombin in the source. Contacting includes, but is not limited to, mixing, admixing and/or adding the source into the $BaSO_4$ or adding the $BaSO_4$ into the source.

In the present invention, it was surprisingly found that prothrombin contact with some $BaSO_4$ reagents triggers conversion into thrombin (i.e. conversion of prothrombin into its intermediates and/or into thrombin). It was found that this is a premature conversion that compromises thrombin yields at the end of the production process.

In some embodiments of the methods described herein, pro-coagulant activity occurs following the conversion of prothrombin into its intermediates and/or into thrombin. Such intermediates may be formed during the proteolytic conversion of prothrombin to thrombin. Non limiting examples of intermediates are prethrombin and meizothrombin.

Some embodiments of the methods described herein enable a $BaSO_4$ reagent suitable for use as prothrombin adsorbents to be identified, preferably prior to use of a given $BaSO_4$ reagent as an adsorbent as part of a full scale thrombin production process.

Specifically, in some embodiments, a sample of a given $BaSO_4$ reagent is contacted with a source of prothrombin to adsorb prothrombin therefrom to obtain $BaSO_4$-adsorbed prothrombin, and subsequently the pro-coagulant activity of the $BaSO_4$-adsorbed prothrombin is evaluated. Typically, the lower the pro-coagulant activity of the $BaSO_4$-adsorbed prothrombin, the more suitable the given $BaSO_4$ reagent is for use as a prothrombin adsorbent. In some embodiments, the suitability of the given $BaSO_4$ reagent for use as a prothrombin adsorbent in a process for preparing thrombin is indicated by the pro-coagulant activity of the $BaSO_4$-adsorbed prothrombin being not greater than the pro-coagulant activity of normal mammalian plasma, e.g. normal human plasma.

Normal mammalian plasma, such as human plasma, is a well-known pooled or single donor plasma preparation intended for use as a calibration plasma for various coagulation tests.

Normal human plasma can be sterile plasma obtained by pooling the liquid portion of whole blood to which has been added a solution of potassium or sodium citrate, or both, e.g.

from eight or more healthy adult humans and by exposing it to ultraviolet light to destroy bacterial and viral contaminants.

Normal human plasma can be Unicalibrator calibration Plasma for Coagulation Tests 00625.

In at least some instances, the methods described herein eliminate the need for selection of a suitable $BaSO_4$ reagent by trial and error.

Some embodiments of the methods described herein are quick and simple to use, and potentially provide saving of time and/or production costs. Some embodiments of the methods described herein allow an increased yield of thrombin from a given source of prothrombin.

Aspects and embodiments of the invention are described in the specification hereinbelow and in the appended claims.

According to an aspect of some embodiments described herein, there is provided a method for the preparation of thrombin from a source of prothrombin using a given $BaSO_4$ reagent as an adsorbent of prothrombin, the method comprising:

a. providing the given $BaSO_4$ reagent and the source of prothrombin;

b. contacting a sample of the given $BaSO_4$ reagent and the source of prothrombin under conditions allowing adsorption of prothrombin from the source of prothrombin by the given $BaSO_4$ reagent thereby obtaining $BaSO_4$-adsorbed prothrombin; and c. evaluating pro-coagulant activity of the $BaSO_4$-adsorbed prothrombin, wherein when the evaluation of c. is carried out by comparing the pro-coagulant activity of the $BaSO_4$-adsorbed prothrombin to a pro-coagulant activity of a normal mammalian plasma, the suitability of the given $BaSO_4$ reagent for use in preparing thrombin is indicated by the pro-coagulant activity of the $BaSO_4$-adsorbed prothrombin being not greater than the pro-coagulant activity of the normal mammalian plasma.

According to a further aspect, provided is a method for the preparation of thrombin from a source of prothrombin using a given $BaSO_4$ reagent as an adsorbent of prothrombin, the method comprising steps a to c above, and further comprising:

d. contacting the suitable $BaSO_4$ with a source of prothrombin under conditions allowing prothrombin adsorption;

e. eluting a prothrombin-containing fraction from the $BaSO_4$-adsorbed prothrombin using an elution buffer;

f. subjecting the eluted fraction to conditions which allow conversion of prothrombin into thrombin, thereby obtaining thrombin.

In some embodiment the method comprises subsequently to step 'e' collecting the eluted fraction.

In some embodiments, the method substantially avoids premature conversion of prothrombin into thrombin. "Premature conversion from prothrombin into thrombin" is meant conversion of prothrombin into thrombin at step 'd'.

Oftentimes, the term "elution" as disclosed herein is interchangeable with the term "desorption".

In one embodiment, the conditions allowing prothrombin adsorption to $BaSO_4$ in the preparation of thrombin comprise pH 7.4-8.6 and/or $BaSO_4$ at a concentration range of about 1%-22% (w/v) e.g. about 1%.

In one embodiment, the elution buffer during the preparation of thrombin comprises calcium chelating salt such as sodium citrate e.g. at a concentration of 3.0-4.4% (w/v) and/or has a pH of between 6.3 and 7.4.

In one embodiment, the conditions which allow conversion of prothrombin into thrombin comprise subjecting the prothrombin to an activator such as calcium ions.

According to a further aspect of some embodiments described herein, there is provided a method for evaluating the suitability of a given $BaSO_4$ reagent for use in preparing thrombin from a source of prothrombin, the method comprising:

a. providing the given $BaSO_4$ reagent and a source of prothrombin;

b. contacting a sample of the given $BaSO_4$ reagent and the source of prothrombin under conditions allowing adsorption of prothrombin from the source of prothrombin to the given $BaSO_4$ reagent thereby obtaining $BaSO_4$-adsorbed prothrombin;

c. evaluating pro-coagulant activity of the $BaSO_4$-adsorbed prothrombin, wherein when the evaluation of c. is carried out by comparing the pro-coagulant activity of the $BaSO_4$-adsorbed prothrombin to a pro-coagulant activity of a normal mammalian plasma, the suitability of the given $BaSO_4$ reagent for use in preparing thrombin is indicated by the pro-coagulant activity of the $BaSO_4$-adsorbed prothrombin being not greater than the pro-coagulant activity of normal mammalian plasma.

According to an aspect of some embodiments of the invention, there is provided a method for the preparation of thrombin from a source of prothrombin using a given $BaSO_4$ reagent as prothrombin adsorbent, the method comprising:

a. providing the given $BaSO_4$ reagent and a source of prothrombin;

b. contacting a sample of the given $BaSO_4$ reagent and the source of prothrombin under conditions allowing adsorption of prothrombin from the source of prothrombin by the given $BaSO_4$ reagent thereby obtaining $BaSO_4$-adsorbed prothrombin; and c. evaluating pro-coagulant activity of the $BaSO_4$-adsorbed prothrombin. In some embodiments, the suitability of the given $BaSO_4$ reagent for use as a prothrombin adsorbent in a process for preparing thrombin is indicated by the pro-coagulant activity of the $BaSO_4$-adsorbed prothrombin being not greater than the pro-coagulant activity of normal mammalian plasma. In some embodiments, the evaluation of c. is carried out by comparing the pro-coagulant activity of the $BaSO_4$-adsorbed prothrombin to a pro-coagulant activity of a normal mammalian plasma, According to an aspect of some embodiments of the invention, there is provided a method for evaluating the suitability of a given $BaSO_4$ reagent for use as a prothrombin adsorbent in preparing thrombin from a source of prothrombin, the method comprising:

a. providing the given $BaSO_4$ reagent and a source of prothrombin;

b. contacting a sample of the given $BaSO_4$ reagent and the source of prothrombin under conditions allowing adsorption of prothrombin from the source of prothrombin by the given $BaSO_4$ reagent thereby obtaining $BaSO_4$-adsorbed prothrombin; and c. evaluating pro-coagulant activity of the $BaSO_4$-adsorbed prothrombin. In some embodiments, the suitability of the given $BaSO_4$ reagent for use as a prothrombin adsorbent in a process for preparing thrombin is indicated by the pro-coagulant activity of the $BaSO_4$-adsorbed prothrombin being not greater than the pro-coagulant activity of normal mammalian plasma. In some embodiments, the evaluation of c. is carried out by comparing the pro-coagulant activity of the $BaSO_4$- adsorbed prothrombin to a pro-coagulant activity of a normal mammalian plasma.

In some embodiments of the methods disclosed herein, evaluating pro-coagulant activity comprises performing a pro-coagulant assay.

In some embodiments of the methods disclosed herein, the pro-coagulant assay comprises a functional assay, such as a functional assay selected from the group consisting of a clotting assay (such as an NAPTT assay, an APTT assay, a protease chromogenic assay or an indicative assay (such as an immunoassay).

In some embodiments, $BaSO_4$ reagents which yielded eluates having an NAPTT ratio of no less than 0.8 were considered suitable for use in the preparation of thrombin.

In some embodiments, $BaSO_4$ reagents which yield eluates having an NAPTT ratio of 0.8 or less or clot are visually observed immediately (clotting occurring upon calcium addition and before clotting time can be recorded in a coagulator measurement machine) are considered non suitable for use in the preparation of thrombin.

In some embodiments of the methods disclosed herein, the source of prothrombin is selected from the group consisting of plasma (such as oxalated plasma) or a plasma fraction. In some such embodiments, the source of prothrombin comprises plasma harvested from a mammal (such as a human, an equine, a bovine and a porcine). In some embodiments, the source of prothrombin comprises porcine plasma. In some embodiments, the source of prothrombin is recombinant prothrombin. In some embodiments, the source of prothrombin is subjected to viral inactivation treatment. For example, the source is solvent/detergent (SD) treated plasma. "Solvent detergent (SD) viral inactivation treatment" typically refers to a process that inactivates enveloped or lipid-coated viruses by destroying their lipid envelope. The treatment can be carried out by the addition of detergents (such as Triton X-45, Triton X-100 or polysorbate 80) and solvents [such as tri(n-butyl) phosphate (TnBP), di- or trialkylphosphates]. The solvent-detergent combination used to deactivate lipid coated viruses may be any solvent-detergent combination known in the art such as TnBP and Triton X-100; polysorbate 80 and Sodium cholate and other combinations.

The concentration of the solvent(s) detergent(s) used can be those commonly used in the art, for example as carried out in U.S. Pat. Nos. 5,094,960A, 4,789,545A. The concentration of the solvent(s) detergent(s) used can be a combination of >0.1% TnBP and >0.1% Triton X-100. The concentration of the solvent(s) detergent(s) used can be a combination of 1% Triton X-100 and 0.3% TnBP. However, other solvent detergent combinations and suitable conditions will be apparent to any person versed in the art.

In one embodiment 0.5% Tween-80 and 0.15% TnBP is used for the SD treatment. The pH is in the range of 7.4-8.6. The solution is incubated at room temperature for 1 hour.

In one embodiment 1% Tween-80 and 0.3% TnBP is used for the SD treatment. The pH is in the range of 7.4-8.6. The solution is incubated at room temperature for 6 hour.

In some embodiments of the methods disclosed herein, contacting the sample of the given $BaSO_4$ reagent and the source of prothrombin comprises adding from about 1% to about 22% or from about 1% to about 10% (w/v) $BaSO_4$ reagent to the source of prothrombin (e.g., harvested plasma). In some embodiments, about 1% (w/v) $BaSO_4$ reagent is added.

In some embodiments, the conditions allowing adsorption of prothrombin from the source of prothrombin by the given $BaSO_4$ reagent comprise pH 7.4-8.6. In some embodiments, the conditions comprise room temperature e.g. in the range of 20° C.-25° C.

The adsorption of prothrombin by $BaSO_4$ reagent can be carried out in batch mode or in a column packed with $BaSO_4$.

In one embodiment, the adsorption of prothrombin by $BaSO_4$ is carried out in batch mode at room temperature e.g. at 25° C. for 2 hours at a pH 7.4-8.6.

In some embodiments of the methods disclosed herein, evaluating pro-coagulant activity of the $BaSO_4$-adsorbed prothrombin is of $BaSO_4$-adsorbed prothrombin while adsorbed to the $BaSO_4$ reagent.

In some embodiments, the methods disclosed herein further comprise, subsequently to 'b' and prior to 'c', eluting at least some of the $BaSO_4$-adsorbed prothrombin from the $BaSO_4$ reagent; and wherein evaluating pro-coagulant activity of the $BaSO_4$-adsorbed prothrombin is of at least some of the eluted $BaSO_4$-adsorbed prothrombin. In some such embodiments, the eluting of at least some of the $BaSO_4$-adsorbed prothrombin from the $BaSO_4$ reagent comprises contacting the $BaSO_4$ reagent with an elution solution at a pH not less than 6.0 and not greater than 7.0.

In some embodiments, the pH of the elution solution is not less than 6.1, not less than 6.2 and even not less than 6.3. In some embodiments, the pH of the elution solution is not more than 6.5, not more than 6.6 and even not more than 6.7, or between about pH 6.3 and 6.7. In some embodiments, the pH of the elution solution is between 6.3 and 7.4.

In some embodiments, the elution solution comprises a chelating salt. In some embodiments, the concentration of chelating salt in the elution solution is from about 0.2% (w/v) to about 4.4% (w/v) or from about 3.0% (w/v) to about 4.4% (w/v). In some embodiments, the chelating salt comprises sodium citrate. In some embodiments, the concentration of the sodium citrate in the elution solution is from about 0.2% (w/v) to about 4.4% (w/v) or from about 3.0% (w/v) to about 4.4% (w/v).

In some embodiments, the given $BaSO_4$ reagent is a reagent comprising at least 75% (w/w) by (weight/weight) $BaSO_4$, for example at least 80%, at least 85%, at least 90%, at least 95%, at least 97.5%, and even at least 88% (w/w) $BaSO_4$.

Unless otherwise defined, all technical and scientific terms used herein have the same meaning as commonly understood by one of ordinary skill in the art to which the invention pertains. In addition, the descriptions, materials, methods, and examples are illustrative only and not intended to be limiting. Methods and materials similar or equivalent to those described herein can be used in the practices of the present invention.

As used herein, the term "given $BaSO_4$ reagent" refers to a $BaSO_4$ reagent from a specified lot of a specified supplier. Different given $BaSO_4$ reagents may therefore be reagents provided by different suppliers, or different lots of reagent provided by the same supplier.

As used herein, the term "pro-coagulant activity" refers to promotion of coagulation of blood. As used herein, the terms "comprising", "including", "having" and grammatical variants thereof are to be taken as specifying the stated features, integers, steps or components but do not preclude the addition of one or more additional features, integers, steps, components or groups thereof. These terms encompass the terms "consisting of" and "consisting essentially of".

As used herein, the indefinite articles "a" and "an" mean "at least one" or "one or more" unless the context clearly dictates otherwise.

As used herein the term "about" refers to ±10%.

BRIEF DESCRIPTION OF THE DRAWINGS

Some embodiments of the invention are described herein with reference to the accompanying figures. The description, together with the figures, makes apparent to a person having ordinary skill in the art how some embodiments of the invention may be practiced. The figures are for the purpose of illustrative discussion and no attempt is made to show structural details of an embodiment in more detail than is necessary for a fundamental understanding of the invention. For the sake of clarity, some objects depicted in the figures are not to scale.

In the Figures.

DESCRIPTION OF SOME EMBODIMENTS OF THE INVENTION

Figure 1:
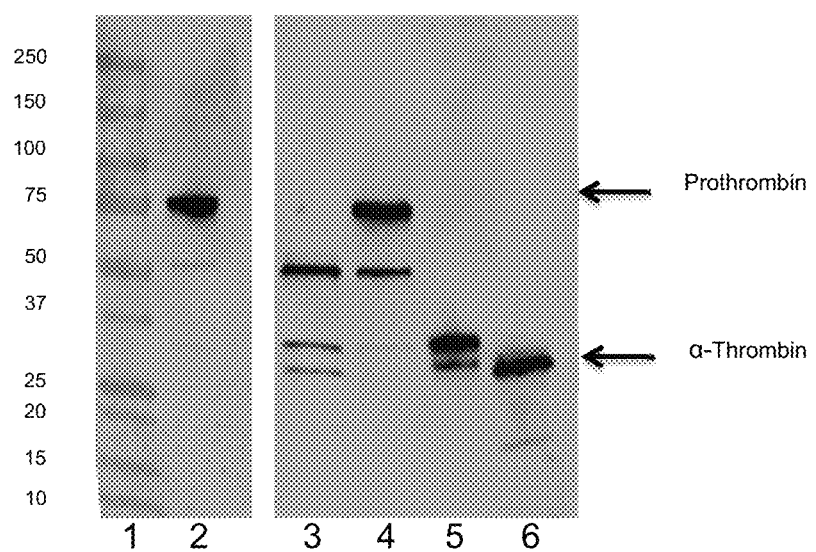
FIG. 1 shows a Western blot analysis of eluants obtained from full scale $BaSO_4$-adsorbed prothrombin samples prepared during production-scale manufacturing of thrombin using $BaSO_4$ reagents from different suppliers.

The invention, in some embodiments thereof, relates to method for the preparation of thrombin from a source of prothrombin using a given $BaSO_4$ reagent as an adsorbent of prothrombin as well as methods for evaluating the suitability of a given $BaSO_4$ reagent for use in preparation of thrombin by contacting the given $BaSO_4$ reagent with a source of prothrombin to obtain $BaSO_4$-adsorbed prothrombin, and evaluating the pro-coagulant activity of the $BaSO_4$-adsorbed prothrombin, in some embodiments, relative to the pro-coagulant activity of normal mammalian plasma.

The principles, uses and implementations of the teachings herein may be better understood with reference to the accompanying description. Upon perusal of the description, one skilled in the art is able to implement the invention without undue effort or experimentation.

Before explaining at least one embodiment in detail, it is to be understood that the invention is not necessarily limited in its application to the details of construction and the arrangement of the components and/or methods set forth in the following description. The invention is capable of other embodiments or of being practiced or carried out in various ways. The phraseology and terminology employed herein are for descriptive purpose and should not be regarded as limiting.

EXAMPLES

Materials and Methods

Materials

Provided were $BaSO_4$ reagents as shown below in Table 1:

TABLE 1

| $BaSO_4$ reagents | | |
|---|---|---|
| Reagent designation | Supplier | Lot no. |
| A | 1 (pharmaceutical grade) | 1 |
| B1 | 2 (pharmaceutical grade) | 1 |
| B2 | 2 (pharmaceutical grade) | 2 |
| C | 3 (pharmaceutical grade) | 1 |
| D1 | 4 (pharmaceutical grade) | 1 |
| D2 | 4 (white std. grade) | 1 |

Sodium Chloride was obtained from Sigma-Aldrich (Cat #S1679, analytical grade, at least 99.0% by weight).

Trisodium Citrate dihydrate was obtained from Sigma-Aldrich Cat #S1804, analytical grade, at least 99.0% by weight). Oxalated porcine blood (including 0.25% (w/w) oxalate solution) was obtained from the abbatoir of Kibbutz Lahav, Israel.

$BaSO_4$-adsorbed prothrombin was obtained during full scale production of thrombin (also referred to herein as full scale samples), wherein the $BaSO_4$ used to adsorb prothrombin was selected from one of the $BaSO_4$-reagents A, B1 defined above in Table 1.

Tween®-80 was obtained from Sigma-Aldrich (Cat #P8074, BioXtra, Polyethylene glycol sorbitan monooleate).

Tri-n-butyl phosphate (TnBP) was obtained from Merck-Millipore (Cat #100002, Pharmaceutical Grade).

Filter 1.2 µm was obtained from Sartorius Stedim India Pvt Ltd., Bangalore, India (Cat #Sartopore® 2 300) and filter 0.45+0.2 µm was obtained from Sartorius Stedim India Pvt Ltd (Cat #Sartopore® 300).

For gel electrophoresis, precast polyacrylamide gels were obtained from Bio-Rad Laboratories Inc. (Mini-gel 4-20% was obtained from Cat. #: 456-1096).

Sheep anti Human Thrombin was obtained from Affinity Biologicals Inc., Canada, (Cat #SAHT-IG)

Anti Sheep IgG alkaline phosphatase conjugate was obtained from Sigma-Aldrich (Cat #A-5187).

Example 1: Preparation of Solvent/Detergent (SD) Viral Inactivated Plasma

Oxalated porcine blood was delivered on ice. The blood was centrifuged at relative centrifugal force (rcf) of 5,000 g (5440 rpm) and temperature of 4° C. for 15 minutes. The supernatant, comprising plasma, was collected, divided into aliquots (300-500 ml) and stored frozen at −30° C. until required.

For preparation of SD treated plasma ("SD plasma"), an aliquot of frozen stored plasma was thawed at 37° C. for approximately 1 hour, then passed through a 1.2 µm filter, then through a 0.45+0.2 µm filter. 0.5% Tween-80 and 0.15% (v/v) TnBP were added for the SD treatment, at pH 7.4-8.6. The solution was stirred at room temperature for 1 hour and the pH was monitored at 7.4-8.6.

Example 2: Preparation of Lab Scale Eluates of $BaSO_4$-Adsorbed Prothrombin from Porcine SD Plasma The SD plasma described above in Example 1 as a source of prothrombin was contacted with samples of the given $BaSO_4$ reagents listed in Table 1.

Specifically, for each one of the six $BaSO_4$ reagents listed in Table 1:

(i) a sample of $BaSO_4$ (1% w/v) reagent was added to a unit of SD plasma.

(ii) The SD plasma/$BaSO_4$ reagent mixture was stirred using a magnetic stirrer at 25° C. for 2 hours (pH 7.4-8.6), allowing adsorption of prothrombin in the SD plasma by the $BaSO_4$ reagent.

(iii) The mixture was centrifuged at 5,000 g (5,440 rpm) at 4° C. for 15 minutes.

(iv) The supernatant and sediment (including $BaSO_4$-adsorbed prothrombin) were separated and each sediment was stored separately at −80° C. until required.

(v) Prior to use, the sediment was thawed for 15 minutes at room temperature (20-25° C.).

(vi) The sediment was resuspended in washing buffer (78 mM NaCl pH 6.9-7.1) at 1:1.4 ratio BaSO$_4$:washing buffer (w/w) and mixed using a tube roller for 15 minutes at room temperature.

(vii) The sediment in washing buffer was then centrifuged at 5,000 g (5,440 rpm) at 4° C. for 15 minutes and the supernatant collected and stored at −80° C. until required. The step was repeated twice (i.e. a total of three washes were carried out).

(viii) Following the washing steps, the washed sediment (including BaSO$_4$-adsorbed prothrombin) was resuspended in elution buffer (3% sodium citrate pH 6.3-6.7) at 1:1.4 ratio BaSO$_4$:elution buffer (w/w) and mixed using a tube roller for 15 minutes.

(ix) The sediment/elution buffer was then centrifuged at 5,000 g (5,440 rpm) at 4° C. for 15 minutes. The prothrombin-containing eluate was collected into a clean container placed on ice, and the elution step was repeated four times (i.e., a total of five elution cycles were performed).

(x) The eluates (containing desorbed prothrombin) from the five elution cycles were combined into a single eluate, filtered through a 0.2 μm PVDF filter and stored in a clean container at −80° C. until tested by NAPTT or Western Blot.

Example 3: Preparation of Full Scale Eluates of BaSO$_4$-Adsorbed Prothrombin from Porcine SD Plasma Full scale samples of frozen prothrombin-adsorbed BaSO$_4$ from porcine plasma were prepared).

BaSO$_4$ reagents used were A and B1 as defined in Table 1.

SD was carried out using 1% Tween-80 and 0.3% TnBP for the SD treatment. The pH was in the range of 7.4-8.6. The solution was incubated with SD for 6 hour at 24-26° C.

In the full scale samples, step v took the place of the corresponding step in lab-scale samples and the sample was processed up to step x.

Example 4: Western Blot Analysis of Prothrombin and Thrombin Content of Eluates

Total protein measurement in each of the eluates (each eluate corresponding to one of the six BaSO$_4$ reagents of Table 1) obtained as described above in Examples 2 and 3 was performed using the Biuret method in order to calculate the loading volume for Western blot assay and to verify that residual unbound proteins and other contaminants were removed by the washing steps (vi and vii).

In order to obtain a better resolution of the proteins from each one of the eluates, proteins from the eluate samples were separated using SDS-PAGE gradient mini precast gel (4%-20%) under reducing conditions. The proteins were transferred from the gel onto a nitrocellulose membrane. Western blot was performed using Sheep anti Human Thrombin and a secondary antibody, Anti Sheep IgG conjugated to alkaline phosphatase.

It was found that some BaSO$_4$-adsorbed prothrombin samples included thrombin (see "Results" section below).

Example 5: Pro-Coagulation Activity of Eluates

Pro-coagulation activity of each one of the eight eluates prepared from porcine SD plasma (6 as in Example 2 and 2 as in Example 3) were evaluated using the Non-Activated Partial Thromboplastin Time (NAPTT) assay, essentially as described in Ph. Eur. (2.6.22). Briefly and as known to a person having ordinary skill in the art, the NAPTT assay comprises concurrently adding phospholipids (Rabbit Brain Cephalin) and calcium ions (as CaCl$_2$) to a tested eluate or adsorbed BaSO$_4$-adsorbed prothrombin sample and to a normal human plasma control [Unicalibrator calibration Plasma for Coagulation Tests 00625] (that inherently contains prothrombin), the calcium ions initiate coagulation in a test sample by conversion of prothrombin to thrombin. The thrombin causes clot formation by conversion of soluble fibrinogen to insoluble fibrin. Clotting time is measured using a Coagulometer (ST ART4 Stago machine).

More specifically, 45 μl of human plasma were added to each of four test wells. For the control samples, 45 μl of TBS/albumin buffer were added to each of two control wells, and 45 μl of diluted test sample were added to each of two additional control wells. 45 μl of Rabbit Brain Cephalin 0.02% solution were then added to each of the four test wells, followed by mixing the content of the wells by gentle shaking and incubation for 1 minute at 37° C. The reaction was started by addition of 45 μl of 0.025 M CaCl$_2$ (previously incubated at 37° C.) into all wells and the clotting time was measured. The NAPTT ratio was calculated as the clotting time (in seconds) of a tested sample divided by the clotting time of the normal human plasma control.

It was found that in eluates in which active thrombin was identified (Example 4), the clotting time was substantially shorter than that of the normal human plasma control. It was found that in some eluates the clotting was immediate. It was found that in some eluates clotting time was above 450 seconds.

It was found that eluates resulting from BaSO$_4$ B1 and B2 gave a high yield of thrombin at the end of the process.

The results indicate that the NAPTT assay can be used for identifying a suitable BaSO$_4$ reagent for thrombin production.

Example 6: Preparation of BaSO$_4$-Adsorbed Prothrombin from Porcine SD Plasma

Steps (i)-(ii) above are repeated for each one of the six BaSO$_4$ reagents in Table 1.

Pro-coagulation activity of a sample of adsorbed BaSO$_4$-adsorbed prothrombin prepared from porcine SD plasma is evaluated using the Non-Activated Partial Thromboplastin Time (NAPTT) assay.

Results

Western Blot Analysis

Western blot analysis of the eluates (Example 3), using BaSO$_4$ reagents A and B1 (Table 1) are presented in FIG. 1.

Lane numbers represent the following:
1—MW ladder
2—Human Prothrombin std.
3—Full scale eluate obtained using BaSO$_4$ reagent A
4—Full scale eluate obtained using BaSO$_4$ reagent B1
5—Human Prethrombin 2 std.
6—Human alpha Thrombin std In FIG. 1, in the full scale eluate obtained using BaSO$_4$ reagent B1 (lane 4), a band corresponding to prothrombin is clearly visible.

In FIG. 1, in the full scale eluate obtained using BaSO$_4$ reagent A (lane 3), a band corresponding to prothrombin is barely visible. Other bands corresponding to prothrombin intermediate proteins as well as alpha thrombin are apparent.

Figure 2:
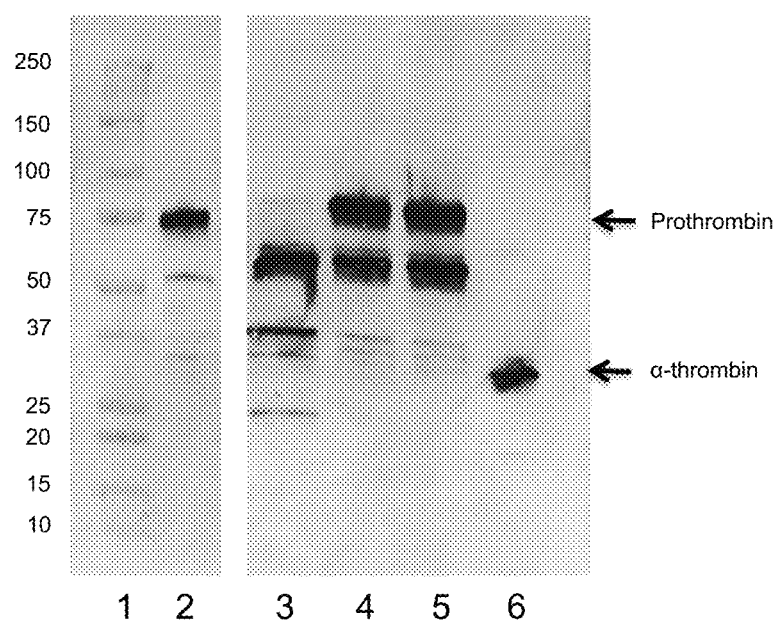
FIG. 2 shows a Western blot analysis of eluants obtained from porcine plasma, prepared using different lots of $BaSO_4$ reagent from the same supplier.

Western blot analysis of eluates obtained from porcine SD plasma (Example 2) using BaSO$_4$ reagents A, B1 and B2 (Table 1) are presented in FIG. 2.

Lane numbers represent the following:
1—MW ladder
2—Human Prothrombin std.
3—Eluate obtained using BaSO$_4$ reagent A
4—Eluate obtained using BaSO$_4$ reagent B1
5—Eluate obtained using BaSO$_4$ reagent B2
6—Human alpha Thrombin std.

The results presented in FIG. 2 show that eluates obtained using different lots of BaSO$_4$ supplied by the same manufacturer (B1—lane 4, B2—lane 5) displayed similar banding patterns. The eluate obtained using BaSO$_4$ reagent A (lane 3) was run as a reference.

Figure 3:
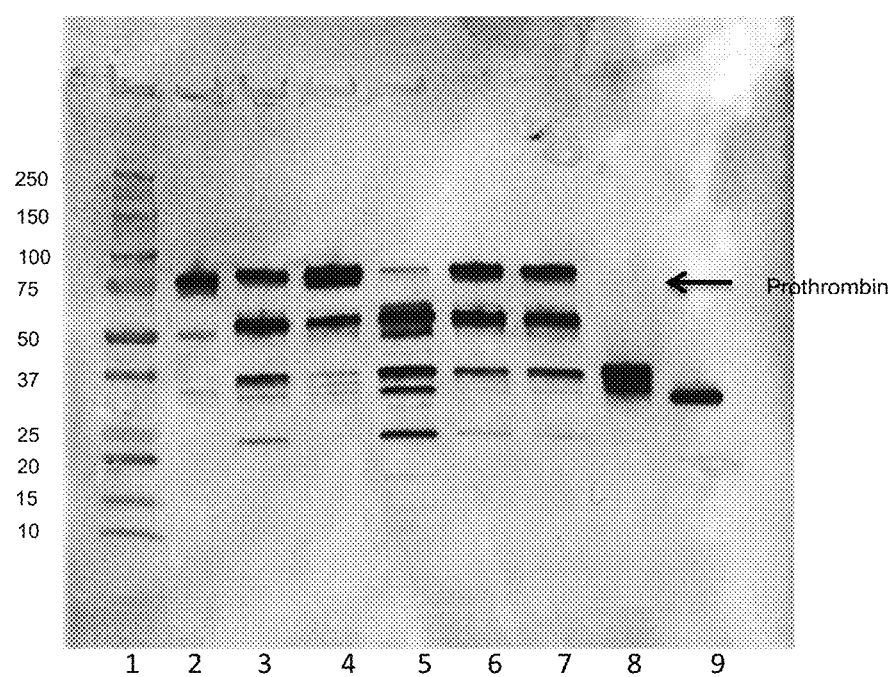
FIG. 3 shows a Western blot analysis of eluants obtained from porcine plasma, prepared using $BaSO_4$ reagents from different suppliers

Western blot analysis of eluates obtained from porcine SD plasma (Example 2) using BaSO$_4$ reagents A, B2, D2, D1 and C are presented in FIG. 3.

Lane numbers represent the following:
1—MW ladder
2—Human Prothrombin std.
3—Eluate obtained using BaSO$_4$ reagent A
4—Eluate obtained using BaSO$_4$ reagent B2
5—Eluate obtained using BaSO$_4$ reagent D2
6—Eluate obtained using BaSO$_4$ reagent D1
7—Eluate obtained using BaSO$_4$ reagent C
8—Human prethrombin 2 std.
9—Human alpha Thrombin std.

The results presented in FIG. 3 show that eluates obtained from porcine SD plasma using pharmaceutical grade BaSO$_4$ (C—lane 7, D1—lane 6) showed similar banding pattern, including bands corresponding with prothrombin and intermediates. This banding pattern was similar to that of eluates obtained using BaSO$_4$ reagent A (lane 3). The eluate obtained with white std grade BaSO$_4$ ("D2"—lane 5) showed a much weaker band corresponding to prothrombin and more intense bands corresponding to intermediates and alpha thrombin. The eluate obtained using reagent B2 (lane 4) showed the most intense prothrombin band and the faintest bands corresponding to intermediates.

NAPPT Assay Results

TABLE 2

Summary of NAPTT assay results

| Prothrombin eluates used | BaSO$_4$ reagent | Clotting time of control (sec) | Clotting time of test sample (sec) |
|---|---|---|---|
| Full scale | A | 308 | Immediate |
| Full scale | B1 | 291 | >450 |
| Lab scale | A | 290 | Immediate |
| Lab scale | B1 | 325 | >450 |
| Lab scale | B2 | 276 | >450 |
| Lab scale | C | 283 | Immediate |
| Lab scale | D1 | 286 | Immediate |
| Lab scale | D2 | 267 | Immediate |

Results of the NAPTT assay for full scale and lab-scale eluates obtained using BaSO$_4$ reagents A, B1, B2, C, D1 and D2 are presented in Table 2.

The results show that irrespective of the prothrombin source, BaSO$_4$ reagents B1 and B2 that were shown to have little or no thrombin by Western Blot caused slower clotting than the control plasma.

The results also show that irrespective of the prothrombin source, BaSO$_4$ reagents A were shown to have a significant thrombin content by Western Blot faster clotting than the control plasma.

Eluates including BaSO$_4$-adsorbed prothrombin obtained from blood plasma using different BaSO$_4$ reagents were analyzed for protein composition using Western Blot and pro-coagulant activity using NAPTT.

The Western blot analysis results (FIG. 1) show differences in banding patterns between eluates from samples obtained using BaSO$_4$ reagents A and B (lanes 3 and 4, respectively). This result suggests that prothrombin in the sample obtained using reagent A had undergone partial conversion to thrombin.

In an NAPTT clotting assay, a clot was formed immediately when testing the eluate obtained using BaSO$_4$ reagent A, whereas in the eluate obtained using reagent B, no clotting was observed even after 450 seconds. It should be noted that normal human plasma is expected to produce a clot in the NAPTT assay within about 200-300 seconds, as indeed was observed as seen in Table 2.

Various different BaSO$_4$ reagents were used to isolate prothrombin from porcine SD plasma and for producing thrombin. Pharmaceutical grade BaSO$_4$ reagents A, C and D1 gave unsatisfactory results like lower-grade BaSO$_4$ reagents A and D2, while some pharmaceutical-grade BaSO$_4$ reagents B1 and B2 provide superior results.

The results showed that the specific BaSO$_4$ reagent used significantly affects the pro-coagulant activity of the BaSO$_4$-adsorbed prothrombin and the yield of thrombin.

It is also shown that at least some of the prothrombin is converted to thrombin and/or thrombin intermediates. The experimental results show that a procoagulation assay can be used as described herein to qualitatively determine whether a given BaSO$_4$ reagent is suitable for use as a prothrombin adsorbent and production of increased yields of thrombin at the end of the process.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination or as suitable in any other described embodiment of the invention. Certain features described in the context of various embodiments are not to be considered essential features of those embodiments, unless the embodiment is inoperative without those elements.

Although the invention has been described in conjunction with specific embodiments thereof, it is evident that many alternatives, modifications and variations will be apparent to those skilled in the art. Accordingly, it is intended to embrace all such alternatives, modifications and variations that fall within the scope of the appended claims.

Citation or identification of any reference in this application shall not be construed as an admission that such reference is available as prior art to the invention.

Example 7: Activation of Prothrombin after Elution of the Prothrombin from the BaSO$_4$ Reagent Prothrombin eluted from BaSO$_4$ A and B1 (as defined in the Table below) was activated as follows:

| Reagent designation | Supplier | Lot no. |
|---|---|---|
| A | 1 (pharmaceutical grade) | 1 |
| B | 2 (pharmaceutical grade) | 1 |

The eluted prothrombin solutions were mixed with $CaCl_2$ (6 g/liter) and Glycine (10 g/liter) and the pH (was adjusted. Next, the solutions were filtered through 0.22 μM Milter and incubated at 20-25° C. for 8 hours followed by incubation at 2-8° C. for up to 72 hours. The thrombin yield obtained using $BaSO_4$ B1 as an adsorbent was about 9 times higher as compared to the yield obtained using $BaSO_4$ A as an adsorbent.

The example demonstrates that it is of advantage to select a suitable $BaSO_4$ reagent prior to full scale thrombin manufacture in order to maximize thrombin yields.

What is claimed is:

1. A method for the preparation of thrombin from a source of prothrombin, the method comprising:
   a. providing one or more $BaSO_4$ reagents and a source of prothrombin;
   b. contacting the one or more $BaSO_4$ reagents and the source of prothrombin under conditions allowing adsorption of prothrombin with the one or more $BaSO_4$ reagents, thereby obtaining $BaSO_4$-adsorbed prothrombin;
   c. testing the pro-coagulant activity of the $BaSO_4$-adsorbed prothrombin, and testing same pro-coagulant activity of normal mammalian plasma source;
   d. evaluating the one or more $BaSO_4$ reagents as suitable $BaSO_4$ adsorbing reagent and selecting a suitable reagent based on said evaluation; wherein the evaluation is carried out by comparing the pro-coagulant activity of the $BaSO_4$-adsorbed prothrombin to the same pro-coagulant activity of a normal mammalian plasma source, the selection of suitable $BaSO_4$ reagent for use in preparing thrombin is based on the pro-coagulant activity of the $BaSO_4$-adsorbed prothrombin being not greater than the pro-coagulant activity of normal mammalian plasma source;
   e. contacting the suitable $BaSO_4$ with a source of prothrombin under conditions allowing prothrombin adsorption;
   f. eluting a prothrombin-containing fraction from the $BaSO_4$-adsorbed prothrombin by contacting the adsorbed prothrombin obtained in step e. with an elution buffer; and
   g. subjecting the eluted fraction to conditions which allow conversion of prothrombin into thrombin, thereby obtaining thrombin.

2. A method for evaluating the suitability of one or more $BaSO_4$ reagents for use as a prothrombin adsorbent in preparing thrombin from a source of prothrombin, the method comprising:
   a. providing one or more $BaSO_4$ reagents and a source of prothrombin;
   b. contacting the one or more $BaSO_4$ reagents and the source of prothrombin under conditions allowing adsorption of prothrombin to the one or more $BaSO_4$ reagents, thereby obtaining $BaSO_4$-adsorbed prothrombin;
   c. testing the pro-coagulant activity of the $BaSO_4$-adsorbed prothrombin and testing same pro-coagulant activity of normal mammalian plasma source; and
   d evaluating the one or more $BaSO_4$ reagents as suitable $BaSO_4$ adsorbing reagents and selecting those suitable reagents based on said evaluation;
   wherein the evaluation is carried out by comparing the pro-coagulant activity of the $BaSO_4$-adsorbed prothrombin to the same pro-coagulant activity of a normal mammalian plasma source, the selection of suitable one or more $BaSO_4$ reagents for use as a prothrombin adsorbant in method of preparing thrombin is based on the pro-coagulant activity of the $BaSO_4$-adsorbed prothrombin being not greater than the pro-coagulant activity of normal mammalian plasma source.

3. The method of claim 2, wherein testing of the pro-coagulant activity comprises performing a pro-coagulant assay.

4. The method of claim 3, wherein the pro-coagulant assay comprises a functional assay.

5. The method of claim 4, wherein the functional assay is a clotting assay.

6. The method of claim 5, wherein the clotting assay is selected from the group consisting of an Non-Activated Partial Thromboplastin Time (NAPTT) assay, an Activated Partial Thromboplastin Time (APTT) assay and a protease chromogenic assay.

7. The method of claim 2, wherein the source of prothrombin is selected from the group consisting of blood plasma and a plasma fraction.

8. The method of claim 7, wherein the blood plasma or plasma fraction comprises oxalated plasma.

9. The method of claim 2, wherein the source of prothrombin comprises plasma harvested from a mammal.

10. The method of claim 9, wherein the mammal is selected from the group consisting of a human, an equine, a bovine and a porcine.

11. The method of any of claim 2, wherein the conditions allowing adsorption of prothrombin from the source of prothrombin by the $BaSO_4$ one or more reagents comprise pH 7.4-8.6.

12. The method of claim 2, wherein contacting the sample of the one or more $BaSO_4$ reagents and the source of prothrombin comprises adding about 1% (w/v) $BaSO_4$ reagent to the harvested plasma that is the source of prothrombin.

13. The method of claim 2, wherein testing of the pro-coagulant activity of the $BaSO_4$-adsorbed prothrombin is performed while the prothrombin is adsorbed to the one or more $BaSO_4$ reagents.

14. The method of claim 2, further comprising:
   subsequently to 'b' and prior to 'c', eluting at least some of the $BaSO_4$-adsorbed prothrombin from the $BaSO_4$ reagent; and
   wherein testing of the pro-coagulant activity of the $BaSO_4$-adsorbed prothrombin is of at least some of the eluted $BaSO_4$-adsorbed prothrombin.

15. The method of claim 14, wherein eluting a prothrombin-containing fraction from the $BaSO_4$-adsorbed prothrombin comprises use of a calcium chelating salt at a pH of about 6.3 and 7.4.

16. The method of claim 15, wherein the chelating salt comprises sodium citrate.

17. The method of claim 16, wherein the concentration of sodium citrate is from about 3% (w/v) to about 4.4% (w/v).

18. The method of claim 2, wherein the source of prothrombin comprises porcine plasma.

* * * * *